US010524754B2

(12) United States Patent
Goshen

(10) Patent No.: US 10,524,754 B2
(45) Date of Patent: Jan. 7, 2020

(54) BONE AND HARD PLAQUE SEGMENTATION IN SPECTRAL CT

(71) Applicant: KONINKLIJKE PHILIPS N.V., Eindhoven (NL)

(72) Inventor: Liran Goshen, Pardes-Hanna (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/463,118

(22) PCT Filed: Nov. 28, 2017

(86) PCT No.: PCT/EP2017/080584
§ 371 (c)(1),
(2) Date: May 22, 2019

(87) PCT Pub. No.: WO2018/099881
PCT Pub. Date: Jun. 7, 2018

(65) Prior Publication Data
US 2019/0282192 A1 Sep. 19, 2019

(30) Foreign Application Priority Data
Nov. 30, 2016 (EP) ..................... 16201419

(51) Int. Cl.
A61B 6/00 (2006.01)
A61B 6/03 (2006.01)
(Continued)

(52) U.S. Cl.
CPC ............ A61B 6/5211 (2013.01); A61B 6/032 (2013.01); A61B 6/481 (2013.01); A61B 6/482 (2013.01);
(Continued)

(58) Field of Classification Search
CPC ....... A61B 6/5211; A61B 6/032; A61B 6/481; A61B 6/482; A61B 6/504; A61B 6/505;
(Continued)

(56) References Cited

U.S. PATENT DOCUMENTS 4,811,373 A * 3/1989 Stein ...................... A61B 6/482
378/146
6,754,298 B2 * 6/2004 Fessler .................. A61B 6/032
378/15
(Continued)

FOREIGN PATENT DOCUMENTS

WO WO2015083065 A1 6/2015

OTHER PUBLICATIONS

Chu et al., 2015, MASCG: Multi-Atlas Segmentation Constrained Graph method for accurate segmentation of hip CT images. (pp. 173-184) (Year: 2015).*

(Continued)

Primary Examiner — Manav Seth
(74) Attorney, Agent, or Firm — Larry Liberchuk

(57) ABSTRACT

The present invention relates to an image processing device (10) comprising a data input (11) for receiving spectral computed tomography volumetric image data organized in voxels, comprising multispectral information for each voxel. The device further comprises a calcium surface feature analyzer (12) for estimating, for each voxel, based on said multispectral information, a first value indicative of a maximum probability that a local neighborhood around the voxel corresponds to a calcium surface structure and a second value indicative of an orientation of the calcium structure surface. The device also comprises a probability processor (13) for calculating a probability map indicative of a probability, for each voxel, that the voxel represents a bone or hard plaque structure, taking at least the first and second (Continued)

value and the multispectral information into account. The device also comprises a segmentation unit (14) for segmenting bone and/or hard plaque structures in the volumetric image data based on the probability map.

15 Claims, 5 Drawing Sheets

(51) Int. Cl.

| | | |
|---|---|---|
| *G06T 11/00* | (2006.01) | |
| *G06T 7/11* | (2017.01) | |
| *G06T 7/143* | (2017.01) | |
| *G06T 7/155* | (2017.01) | |
| *G16H 30/40* | (2018.01) | |
| *G06T 7/149* | (2017.01) | |

(52) U.S. Cl.
CPC ............... *A61B 6/504* (2013.01); *G06T 7/11* (2017.01); *G06T 7/143* (2017.01); *G06T 7/155* (2017.01); *G06T 11/008* (2013.01); *G16H 30/40* (2018.01); *A61B 6/505* (2013.01); *G06T 7/149* (2017.01); *G06T 2207/10081* (2013.01); *G06T 2207/30008* (2013.01); *G06T 2211/408* (2013.01)

(58) Field of Classification Search
CPC . G06T 7/143; G06T 7/11; G06T 7/155; G06T 11/008; G06T 7/149; G06T 2207/10081; G06T 2207/30008; G06T 2211/408; G16H 30/40
See application file for complete search history.

(56) References Cited

U.S. PATENT DOCUMENTS

| | | | | |
|---|---|---|---|---|
| 7,457,450 | B2* | 11/2008 | Bruder | A61B 6/032 378/4 |
| 7,477,768 | B2* | 1/2009 | Kaufman | G06T 7/0012 378/41 |
| 7,889,834 | B2* | 2/2011 | Heismann | G06T 11/005 378/4 |
| 7,920,735 | B2* | 4/2011 | Krauss | A61B 6/482 378/21 |
| 8,542,230 | B2* | 9/2013 | Krauss | A61B 6/032 345/424 |
| 8,649,577 | B1* | 2/2014 | Arnold | A61B 6/025 382/128 |
| 9,153,045 | B2* | 10/2015 | Polster | A61B 6/505 |
| 9,311,570 | B2* | 4/2016 | Mohr | G06T 7/136 |
| 9,547,889 | B2* | 1/2017 | Goshen | G06T 5/002 |
| 9,710,880 | B2* | 7/2017 | Xu | G06T 11/003 |
| 9,905,044 | B1* | 2/2018 | Carmi | G06T 15/08 |
| 9,964,499 | B2* | 5/2018 | Masood | G01N 23/046 |
| 9,990,712 | B2* | 6/2018 | Gazit | G06T 7/11 |
| 10,282,820 | B2 | 5/2019 | Goshen | |
| 2005/0228272 | A1 | 10/2005 | Yu | |
| 2008/0253508 | A1* | 10/2008 | Krauss | A61B 6/032 378/19 |
| 2011/0033099 | A1 | 2/2011 | Kadomura | |
| 2011/0064292 | A1 | 3/2011 | Chen | |
| 2014/0133729 | A1* | 5/2014 | Goshen | G06T 5/002 382/131 |
| 2016/0300343 | A1* | 10/2016 | Gazit | G06T 7/11 |
| 2016/0307330 | A1* | 10/2016 | Goshen | G06T 5/002 |

OTHER PUBLICATIONS

PCT International Search Report, International application No. PCT/EP2017/080584, Feb. 1, 2018.

Frangi A F et al., "Multiscale Vessel Enhancement Filtering", Electronic Publishing, Artistic Imaging, and Digital Typography; [Lecture Notes in Computer Science, Springer Verlag, DE, vol. 1496, 1998, pp. 130-137, XP002345875.

Goshen, L., et al., "An Iodine-Calcium Separation Analysis and Virtually Non-Contrasted Image Generation Obtained with Single Source Dual Energy MDCT", In IEEE Nucl Sci Symp Conf Rec, Oct. 2008, pp. 3868-3870.

Vogel C. R. et al., "Computational Methods for Inverse Problems", SIAM, Series: Frontiers in Applied Mathematics, 2002.

Osher S. et al., "An Iterative Regularization Method for Total Variation-Based Image Restoration." Multiscale Modeling & Simulation 4.2, 2005, pp. 460-489.

Caselles V. et al., "Geodesic Active Contours", IEEE International Conference on Computer Vision, vol. 22, issue 1, pp. 61-79, 1997.

\* cited by examiner

BONE AND HARD PLAQUE SEGMENTATION IN SPECTRAL CT

FIELD OF THE INVENTION

The invention relates to the field of digital image processing. More specifically it relates to the segmentation of bone and/or hard plaque structures in spectral computed tomography (CT) image data.

BACKGROUND OF THE INVENTION

In computed tomography (CT), images that reveal the internal structure of an object under study can be obtained by means of penetrating ionizing radiation. Such image, e.g. three-dimensional volumetric image data, can be obtained by applying reconstruction techniques, as known in the art, to projection images obtained by a detector and corresponding to different orientations of a source of penetrating ionizing radiation and the detector with respect to the object, e.g. corresponding to different directions of projecting radiation through the object. The reconstructed image data may be organized in voxels, representative of different positions in the object with respect to a three-dimensional coordinate system, and each voxel may have a value associated therewith, e.g. a greyscale value such as a value expressed in Hounsfield units, that is indicative of attenuation characteristics of the scanned object at the position corresponding to the voxel, e.g. indicative of a radio density, e.g. of a relative radio density.

Spectral CT is an imaging modality that extends the capabilities of conventional CT. In spectral CT, each voxel value may be determined for at least two different qualities of penetrating ionizing radiation. Thus, at least two different attenuation characteristics, e.g. greyscale values, can be assigned to each pixel concurrently. The different qualities of penetrating ionizing radiation may for example differ sufficiently in mean and/or peak photon energy such that the different attenuation characteristics may be subject to discernibly different photoelectric effect and Compton effect contributions, enabling a good differentiation of different materials within the object.

Spectral CT is for example used in medical applications for non-invasively inspecting the internal structure of the body of a subject. Furthermore, spectral CT may be particularly suitable for quantitative imaging applications, since the additional spectral information improves the quantitative information that can be measured about the scanned object and its material composition.

Medical applications of spectral CT, for example vessel analysis or trauma applications, may commonly require a segmentation of bone and/or hard plaque structures in the image data. For example, a segmentation of bone and/or hard plaque structures may enable a selective removal of such structures from the image to enable a better view, or a further automated analysis, of the other structures registered in the image data, such as organs, vessels or other soft tissues of interest.

Segmentation approaches, as known in the art, may be based on time consuming and tedious semi-automatic methods, which may rely of topological background information, such as atlas based methods. Furthermore, interactive editing tools may be used to correct and/or adjust the results of such semi-automatic procedure. However, methods for segmenting bone and/or hard plaque structures known in the art may have the disadvantage of only providing a limited level of precision.

For example, methods known in the art may predominantly rely on simple density or gradient operators. Such methods may provide limited precision and reliability in bone and/or hard plaque segmentation due to different materials having a similar density range while also being near each other. For example bones and vessels may lie in close spatial proximity and may present similar greyscale values in the acquired CT images, e.g. when an intravenously injected contrast agent is used.

For example, accurately and reliably segmenting a bone structure in CT image data, even when using the spectral information gain provided by spectral CT images, may be particularly challenging, since bone structures may have a complex structure and a heterogeneous material composition. For example, some bone and plaque structures, e.g. the trabecular bone, may be complex structures that not only comprise calcium, but also, to a substantial degree, other materials, e.g. soft tissue and adipose tissue. Therefore, the attenuation and spectral characteristics of such bone or plaque structures may be very similar to other structures in the body, e.g. to contrast enhanced organs.

Furthermore, while allowing more information with respect to the constituent materials of the scanned object to be gained as compared to conventional CT, and thus, in principle, enabling a good differentiation of the materials, spectral CT image acquisition may have inherent image quality issues, such as enhanced noise. Thus, bone segmentation algorithms that are based mostly on spectral information may deliver suboptimal results.

For example, WO 2015/083065 discloses a prior art method for segmenting bone in spectral image data. The spectral image data includes at least a first set of image data corresponding to a first energy and second set of image data corresponding to a second different energy. The method includes obtaining the spectral image data. The method further includes extracting a set of features for each voxel in spectral image data. The method further includes determining, for each voxel, a probability that each voxel represents bone structure based on the set of features. The method further includes extracting bone structure from the spectral image data based on the probabilities.

SUMMARY OF THE INVENTION

It is an object of embodiments of the present invention to provide fast, automatic, accurate, reliable and/or robust segmentation of bone and/or hard plaque structures in spectral CT image data.

The above objective is accomplished by a method and device according to the present invention.

It is an advantage of embodiments of the present invention that robust, reliable and/or accurate segmentation can be achieved even for atypical bone and/or hard plaque structures, e.g. abnormal bone structures. It is a further advantage that good segmentation can be achieved without requiring topological prior knowledge, such as a reference atlas of bone structures.

It is an advantage of embodiments of the present invention that good segmentation and/or removal can be achieved of bone and/or hard plaque structures in spectral CT volumetric images to enable an efficient workflow in radiology, e.g. in vessel evaluation, trauma evaluation and/or orthopedic applications.

It is an advantage of embodiments of the present invention that bone and/or hard plaque can be segmented accurately where structures, such as bones and vessels, that have a similar density range and that lie in close proximity to each other could complicate a conventional segmentation approach based solely on simple density and/or gradient operators.

It is an advantage of embodiments of the present invention that bone can be segmented accurately despite a complex bone structure and a heterogeneous material composition of bone.

It is an advantage of embodiments of the present invention that bone can be segmented accurately despite having attenuation and spectral characteristics similar to other structures in the body, such as contrast enhanced organs and/or vessels.

It is an advantage of embodiments of the present invention that the use of spectral CT volumetric image data allows a good differentiation of constituent materials in a scanned object, e.g. of bone and iodine, than conventional CT, and thus also a good quality segmentation.

It is an advantage of embodiments of the present invention that image quality issues inherent to spectral CT, such as enhanced noise, can be overcome such as to provide a good quality segmentation by determining a probability of bone and/or hard plaque presence using measures indicative of morphological features, texture features and/or other features relating to local structure, e.g. as opposed to determining such measure of probability merely on the basis of a scalar grey value distribution and/or a bivariate spectral CT grey value distribution.

In a first aspect, the present invention relates to an image processing device that comprises a data input for receiving spectral computed tomography volumetric image data organized in voxels, said volumetric image data comprises multispectral information for each voxel. The device comprises a calcium surface feature analyzer for estimating, for each voxel of the volumetric image data and based on said multispectral information, a first value indicative of a maximum probability that a local neighborhood around the voxel corresponds to a calcium surface structure, e.g. a calcium structure surface, and a second value indicative of an orientation of the calcium surface structure that corresponds to this maximum. The device also comprises a probability processor for calculating a probability map indicative of a probability, for each voxel of the volumetric image data, that the voxel represents a bone or hard plaque structure, taking at least the first value, the second value and the multispectral information into account. The device furthermore comprises a segmentation unit for segmenting bone and/or hard plaque structures in the volumetric image data based on the probability map.

In an image processing device in accordance with embodiments of the present invention, the probability processor and the calcium surface feature analyzer may be adapted for performing a multi-scale analysis, in which the probability, for each voxel of the volumetric image data, that the voxel represents a bone or hard plaque structure is determined at a plurality of different scales, and in which the probability map is determined by, for each voxel, selecting the maximum probability over the plurality of different scales.

In an image processing device in accordance with embodiments of the present invention, the calcium surface feature analyzer may be adapted for generating a calcium map based on the multispectral information for each voxel, e.g. each pixel, in the spectral CT volumetric image data, wherein the calcium map comprises, for each voxel of the volumetric image data, a value indicative of a calcium content at the corresponding voxel location. The first value and the second value may thus be estimated based on this calcium map.

In an image processing device in accordance with embodiments of the present invention, the calcium surface feature analyzer may be adapted for determining the first value, for each voxel, as a maximum of probabilities, in which each of the probabilities represents a probability of the local neighborhood around the voxel in the calcium map to match a corresponding predetermined surface template.

In an image processing device in accordance with embodiments of the present invention, the probability processor may be adapted for determining the probability, for each voxel of the volumetric image data, that the voxel represents a bone or hard plaque structure by combining a plurality of probabilities indicative of spectral information and morphological features around each voxel.

In an image processing device in accordance with embodiments of the present invention, the probability processor may be adapted for combining the plurality of probabilities by multiplication.

In an image processing device in accordance with embodiments of the present invention, the probability processor may be adapted for combining the plurality of probabilities for each scale of the plurality of scales separately.

In an image processing device in accordance with embodiments of the present invention, the probability processor may be adapted for computing the plurality of probabilities indicative of spectral information and morphological features around each voxel, in which the plurality of probabilities comprises the first value indicative of the maximum probability that a local neighborhood around the voxel corresponds to a calcium surface structure and any one of, or any combination of, preferably all, the following:

a probability of the voxel being at a volumetric ridge in the calcium map taking the second value into account, a probability of the voxel to include calcium and not iodine, wherein this probability may be determined based on the multispectral information, a probability that a neighborhood of the voxel has a spectral response that is different from a spectral response of iodine, wherein this probability may be based on the multispectral information, and a probability of a neighborhood of the voxel to have a bone or a hard plaque texture.

In an image processing device in accordance with embodiments of the present invention, the probability processor may furthermore be adapted for calculating a regularized map based on the probability map, wherein calculating the regularized map comprises a joint optimization of at least:

a fidelity measure representative of a difference between said regularized map and said probability map, and a regularization penalty.

In an image processing device in accordance with embodiments of the present invention, the regularization penalty may comprise any one of, or any combination of, preferably all of, the following:

a penalty for inhomogeneous spatial distribution of the regularized map, a penalty for inhomogeneous spatial distribution of the gradient magnitude of the regularized map, and a penalty for local inhomogeneity of the regularized map along the local surface orientation defined by said second value.

In an image processing device in accordance with embodiments of the present invention, the probability processor may be adapted for calculating the regularized map using variational optimization of a functional.

In an image processing device in accordance with embodiments of the present invention, the segmentation unit may be adapted for applying a geometric active contour approach to the regularized map.

In a second aspect, embodiments of the present invention also relate to a computed tomography workstation comprising an image processing device in accordance with embodiments of the first aspect of the present invention.

In a further aspect, embodiments of the present invention also relate to a method for processing spectral computed tomography volumetric image data, the method comprising:

obtaining spectral computed tomography volumetric image data organized in voxels, said volumetric image data comprises multispectral information for each voxel;

estimating, for each voxel of said volumetric image data and based on said multispectral information, a first value indicative of a maximum probability that a local neighborhood around said voxel corresponds to a calcium surface structure and a second value indicative of an orientation of said calcium surface structure that corresponds to said maximum;

calculating a probability map indicative of a probability, for each voxel of said volumetric image data, that said voxel represents a bone or hard plaque structure, taking at least said first value, said second value and said multispectral information into account; segmenting bone and/or hard plaque structures in said volumetric image data based on said probability map.

In a yet further aspect, embodiments of the present invention also relate to a computer readable storage medium encoded with one or more computer executable instructions, which, when executed by a processor of a computing system, causes the computing system to perform a method in accordance with embodiments of the present invention.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
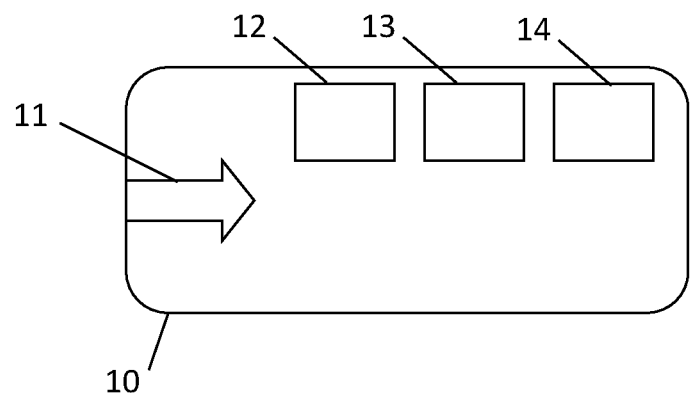
FIG. 1 shows an image processing device in accordance with embodiments of the present invention.

The drawings are only schematic and are non-limiting. In the drawings, the size of some of the elements may be exaggerated and not drawn on scale for illustrative purposes.

Any reference signs in the claims shall not be construed as limiting the scope. In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description. In a first aspect, embodiments of the present invention relate to an image processing device that comprises a data input for receiving spectral computed tomography volumetric image data organized in voxels. This volumetric image data comprises multispectral information for each voxel, e.g. the volumetric image data may comprise, for each voxel, a plurality of scalar values representative of attenuation properties in that voxel for a corresponding plurality of different spectra of ionizing radiation.

The image processing device further comprises a calcium surface feature analyzer for estimating, for each voxel of the volumetric image data and based on said multispectral information, e.g. based on said multispectral information for each voxel, a first value indicative of a maximum probability that a local neighborhood around the voxel corresponds to a calcium surface structure, e.g. to a surface of a calcium rich structure.

The image processing device also comprises a probability processor for calculating a probability map indicative of a probability, for each voxel of the volumetric image data, that the voxel represents a bone or hard plaque structure, taking the first value, the second value and the multispectral information into account. The image processing device further comprises a segmentation unit for segmenting bone and/or hard plaque structures in the volumetric image data based on the probability map.

FIG. 1 illustrates an exemplary image processing device 10 in accordance with embodiments of the present invention. The image processing device may comprise a computing device, such as a computer programmed for providing the functionality as described herein below. The computing device may comprise a configurable hardware device, e.g. a field-programmable gate array, configured for providing the intended functionality or may comprise application specific circuitry specifically designed for providing the intended functionality. The computing device may comprise any combination of designed hardware, configured hardware and/or software for executing on general purpose hardware.

Thus, components of an image processing device 10 in accordance with embodiments of the present invention, such as a data input, calcium surface feature analyzer, a probability processor and/or a segmentation unit, do not necessarily correspond to physically separate entities of such device, e.g. physically separable components, but may refer to a software construct that is implemented in a computer code for executing on a general purpose computer.

The image processing device 10 comprises a data input 11 for receiving spectral computed tomography (CT) volumetric image data organized in voxels. Particularly, the data input may comprise a digital communication circuit, such as a computer network interface, a wireless transmission interface or a digital data bus interface, for receiving the data from an external source, such as a spectral CT scanner or a reconstructor for reconstructing CT images provided by a spectral CT scanner. The data input may comprise a virtual interface for receiving the data from another software component implemented on a shared hardware platform, e.g. from another software component executing on the same computer, such as a software component for reconstructing spectral CT image data. Such virtual interface may for example comprise an application programming interface, a shared memory resource or a file stored using a filesystem standard on a data carrier. The data input may comprise an interface for accessing a data carrier, such as an optical disk reader, a universal serial bus (USB) connection for accessing a USB data storage medium, a magnetic disk reader or a portable flash drive reader. The data input may comprise any combination of the means mentioned hereinabove, and/or other devices known in the art suitable for receiving digital volumetric image data.

The spectral CT volumetric image data is organized in voxels, e.g. comprising a plurality of data values linked to corresponding voxel locations in a scanned object, e.g. a scanned subject. The spectral CT volumetric image data may thus comprise reconstructed image data organized in voxels, e.g. representative of different positions in the scanned object with respect to a three-dimensional coordinate system. Each voxel may have a value associated therewith, e.g. a greyscale value such as a value expressed in Hounsfield units, that is indicative of attenuation characteristics of the scanned object at the position corresponding to the voxel, e.g. indicative of a radio density, e.g. of a relative radio density. Each voxel value may be determined for at least two different qualities of penetrating ionizing radiation. Thus, at least two different attenuation characteristics, e.g. greyscale values, may be assigned to each voxel concurrently. The different qualities of penetrating ionizing radiation may for example differ sufficiently in mean and/or peak photon energy such that the different attenuation characteristics may be subject to discernibly different photoelectric effect and Compton effect contributions, enabling a good differentiation of different materials within the object. The spectral CT volumetric image data may thus comprise, for each voxel location, at least a scalar value corresponding to a first energy distribution of ionizing radiation and a second scalar value corresponding to a second energy distribution. Thus, the spectral CT volumetric image data may include at least a first set of image data corresponding to a first energy and a second set of image data corresponding to a second different energy. The volumetric image data may also comprise virtual monochromatic images. For example the first and second scalar value per voxel may, in some embodiments, correspond to an arbitrary basis decomposition, as opposed to corresponding to physical energy spectra of ionizing radiation and/or detector characteristics used in scanning the object. The first and second scalar value may form a coordinate pair (a, b) in a spectral space, e.g. the image data may define for each voxel location (x,y,z) in a spatial space a coordinate pair (a,b) in spectral space. Here, the reference to 'spectral space' does not imply any connection to a spectral analysis of a corresponding temporal or spatial signal, but merely refers to the codomain of a spectral CT imaging operation that conveys both mass density and effective atomic number information of absorber materials and that may be parametrized in any suitable basis, such as by a 80 kVp and a 120 kVp component image, by a water-material and a bone-material image, by at least two monochromatic virtual images, etc.

The spectral CT volumetric image data may for example comprise Dual-Energy (DE) CT volumetric image data. The image data may be acquired, e.g. pre-recorded, using a spectral CT scanning technique known in the art, e.g. a dual energy scan approach as known in the art, such as acquisition using a scanner having a dual-source configuration, a scanner adapted for fast kVp switching while scanning or a scanner having a dual-layer detector configuration.

The image processing device further comprises a calcium surface feature analyzer 12 for estimating, for each voxel of the volumetric image data, a first value indicative of a maximum probability that a local neighborhood around the voxel corresponds to a calcium surface structure, e.g. to a surface of a calcium rich structure. It is an advantage of spectral CT that calcium can be distinguished from other materials having similar attenuation characteristics, e.g. from iodine. Thus surface structures can be more easily detected, e.g. particularly where such surface structures are adjacent to, for example, a contrast enhanced fluid in a vessel.

The calcium surface feature analyzer 12 may be adapted for generating a calcium map based on the multispectral information for each voxel, e.g. each pixel, in the volumetric image data. For example, this map may comprise, for each voxel of the volumetric image data, a value indicative of the calcium content in the scanned object at the corresponding voxel location. The first value and the second value may thus be estimated based on this calcium map. For example, the spectral information in the volumetric image data may be used to extract such calcium map. For example, the volumetric image data may be represented as a pair of values (a,b) in each voxel location, and in the space of these coordinates (a,b), reference lines may be defined that are representative for calcium-like materials, soft-tissue-like materials and iodine-like materials. Thus each voxel entry of the calcium map may be estimated as a minimum between projections of the pair (a,b) along the calcium reference line to the soft tissue reference line and to the iodine reference line. For example, the calcium map may be determined in accordance with the equation:

$$Map_{ca} = \min(Map_{ca\backslash soft}, Map_{ca\backslash io})$$

where $Map_{x\backslash y}$ can be obtained by projecting each voxel along the x material line to the y material line, and where 'ca.' represents the calcium, 'soft' represents the soft tissue and 'io' represents the iodine material.

The first value may be determined as a maximum probability that a local structure in the calcium map, around a voxel, fits a structure of a surface. For example, this maximum probability may be determined as a maximum of probabilities, in which each of these probabilities represents a probability of the local structure matching a corresponding predetermined surface template.

For example, the first value $prob^{ncc}$ may represent a probability of the local structure around a calcium map voxel to fit a structure of a surface. This probability may be estimated, for example, by computing a maximum normalized cross-correlation of a sub-volume around a voxel over a plurality of matrix surface templates, e.g. as follows:

$$prob^{ncc} = \max_j \{ncc(Map_{ca}, template_j)\}_{j=1}^{n_t}$$

where a plurality of surface templates $template_j$, e.g. $n_t$ different surface templates, for example characterized by different surface orientations, may be individually matched to the local voxel neighborhood in the calcium map. The first value may thus be elected as the normalized cross-correlation measure corresponding to the best-fit surface template, e.g. the highest normalized cross-correlation measure that was achieved for that voxel over the plurality of templates. Furthermore, this first value may be determined for a plurality of scales, e.g. as $$prob_i^{ncc} = \max_j \{ncc(Map_{ca}, template_j)\}_{j=1}^{n_t}$$

where the index i refers to a particular scale, e.g. an analysis at a scale obtained by scaling the volumetric image data by a factor $(\frac{1}{2})^{i-1}$, as will also be clear in relation to a multiscale analysis for calculating a probability map as described herein below. Otherwise said, the first value per voxel may comprise a plurality of values corresponding to the voxel analyzed at different scales. For example, each scale may correspond to a different size selection of the local neighborhood of the voxel that may be matched to surface templates. It is an advantage of such multiscale approach that, while detection of surface structures at a small scale may be more difficult due to noise present in the image data, a more robust detection of surface structures, and the associated probability of being part of a surface structure, can be achieved at larger scales. On the other hand, strongly curved on convoluted surface structures may not be easily detectable at larger scales, for example when flat surface templates are used, yet may advantageously still be detectable at smaller scales. The calcium surface feature analyzer 12 may also be adapted for estimating, for each voxel of the volumetric image data, a second value indicative of an orientation of the calcium surface structure that corresponds to this maximum probability. For example, similar to the example for calculating the first value hereinabove, $$\underset{j}{\operatorname{argmax}} \{ncc(Map_{ca}, template_j)\}_{j=1}^{n_t}$$

may be calculated and used to determine, for each voxel, the orientation of the surface that corresponds to the best surface template fit for the local neighborhood of the voxel. Likewise, for a multiscale approach, this second value indicative of a most likely surface orientation may be determined over the plurality of scales, e.g. using $$\underset{j}{\arg\max} \{\{ncc(Map_{ca}^i, template_j)\}_{j=1}^{n_t}\}_{i=1}^{n_s}$$

Where $Map_{ca}^i$ refers to the calcium map computed, or scaled at, a scale i and $n_s$ refers to the number of analyzed scales.

The image processing device also comprises a probability processor 13 for calculating a probability map indicative of a probability, for each voxel of the volumetric image data, that the voxel represents a bone or hard plaque structure, by taking at least the first value into account.

The probability processor 13 may be adapted for performing a multi-scale analysis, in which the probability, for each voxel of the volumetric image data, that the voxel represents a bone or hard plaque structure is determined at a plurality of different scales. For example, the probability map may be determined by selecting the maximum probability that the represents a bone or hard plaque structure over a plurality of scales.

For example, the probability map may be determined in accordance with the equation:

$$\text{Map}_{prob} = \max_i \{\text{Map}_{prob}^i\}_{i=1}^n$$

where $\text{Map}_{prob}^i$ may be an intermediate probability map for a corresponding scale i. The multiscale analysis may be performed by appropriately scaling down the image data relied upon, e.g. the volumetric image data and/or a calcium map determined by the calcium surface feature analyzer, by a factor, for example, a factor $(\frac{1}{2})^{i-1}$, and determining an intermediate probability map $\text{Map}_{prob}^i$ at that scale, or, alternatively, by determining a single intermediate probability map $\text{Map}_{prob}^1$, e.g. at the scale of the input volumetric image data, scaling down this intermediate probability map, by factors $(\frac{1}{2})^{i-1}$, and applying the maximization referred to hereinabove over the thereby obtained scales. Alternatively or additionally, another multiscale analysis approach as known in the art may be used, e.g. by applying a scale-space decomposition, e.g. a wavelet decomposition, of the input image data, the calcium map and/or an intermediate probability map.

The probability processor 13 may be adapted for determining the probability, for each voxel of the volumetric image data, that the voxel represents a bone or hard plaque structure by combining a plurality of probabilities indicative of spectral information and morphological features around each voxel. This combining may comprise a multiplication, e.g. a voxel elementwise multiplication or Hadamard product, of the plurality of probabilities, e.g.

$$\text{prob}_i = \text{prob}_i^{ca/io} \cdot \text{prob}_i^{ncc} \cdot \text{prob}_i^{ridge} \cdot \text{prob}_i^{texture} \cdot \text{prob}_i^{dist}.$$

This combining of the plurality of probabilities may be performed for each scale separately, e.g. to compute an intermediate probability map $\text{Map}_{prob}^i$, e.g. to compute each intermediate probability map separately.

The plurality of probabilities indicative of spectral information and morphological features around each voxel may comprise the first value indicative of the maximum probability that a local neighborhood around the voxel corresponds to a calcium surface structure, e.g. $\text{prob}_i^{ncc}$ as described hereinabove.

The plurality of probabilities indicative of spectral information and morphological features around each voxel may comprise a probability $\text{prob}_i^{ridge}$ of the voxel being at a volumetric ridge in the calcium map. The probability of the voxel being at a volumetric ridge in the calcium map may be determined based on the second value indicative of the orientation of the calcium structure surface, e.g. indicative of the most likely orientation of the surface of a calcium structure when present at the voxel location. For example, the probability $\text{prob}_i^{ridge}$ may be estimated by setting the probability to one if the voxel corresponds to a local maximum of the calcium map in the direction that is orthogonal to the surface template for which the maximum value was obtained in determining the first value, as described hereinabove. Otherwise, the probability may, for example, be set to a lower value, e.g. to zero.

The plurality of probabilities indicative of spectral information and morphological features around each voxel may comprise a probability $\text{prob}_i^{ca/io}$ of the voxel to include calcium and not iodine, based on said multispectral information. This probability may be estimation, for example, as follows:

$$\text{prob}_i^{ca/io} = \frac{dist(io)^2}{dist(io)^2 + dist(ca)^2}$$

where dist(x) is a distance, in the spectral space, e.g. in the coordinate space of spectral characteristics (a,b), of a voxel to the material line x.

The plurality of probabilities indicative of spectral information and morphological features around each voxel may also comprise a probability $\text{prob}^{dist}$ of a neighborhood of the voxel having a spectral response that is different from a spectral response of iodine. This probability could be estimated, for example, as follows:

$$\text{prob}_i^{dist} = \frac{1}{1 + e^{-s_d(stdfilt(dist(io))-b_d)}}$$

where $s_d$ and $b_d$ are control parameters, e.g. which may be set to predetermined values or selected by straightforward optimization.

The plurality of probabilities indicative of spectral information and morphological features around each voxel may also comprise a probability $\text{prob}_i^{texture}$, that represents a probability of a neighborhood of the voxel to have a bone or a hard plaque texture. This probability may be estimated, for example, as follows:

$$\text{prob}_i^{texture} = \frac{1}{1 + e^{-s_t(stdfilt(Map_{ca})-b_t)}}$$

where $s_t$ and $b_t$ are control parameters, e.g. which may be set to predetermined values or selected by straightforward optimization, $\text{Map}_{ca}$ refers to the calcium map, and stdfilt(·) is the standard deviation of a neighborhood of the voxel at hand. It shall be clear to the skilled person that this probability related to a texture is not necessarily limited to this example, but may equally relate to other measures for matching a texture to a local region around the voxel at hand that are known in the art. For example, the probability may be determined by any suitable function mapping a zero deviation between stdfilt($\text{Map}_{ca}$) and $b_t$ to a probability of one, while mapping an arbitrary large value of this deviation to a probability of substantially zero. Likewise, a deviation of a higher statistical moment, e.g. a skewness or kurtosis, to a reference value for bone and/or hard plaque may be similarly considered in such texture probability measure.

The probability processor 13 may furthermore be adapted for calculating a regularized map based on said probability map, e.g. for restoration of a bone and hard plaque map based on the probability map $\text{Map}_{prob}$. Calculating this regularized map may comprise a joint optimization of at least (i) a fidelity measure representative of a difference between said regularized map, e.g. the bone and hard plaque map, and the probability map $\text{Map}_{prob}$, and (ii) a regularization penalty.

The regularization penalty may comprise a penalty for inhomogeneous spatial distribution of the regularized map, a penalty for inhomogeneous spatial distribution of a gradient magnitude of the regularized map and/or a penalty for local inhomogeneity of the regularized map along the local surface orientation defined by the second value referred to hereinabove.

The probability processor 13 may be adapted for calculating the regularized map using a technique known in the art for map restoration, such as, for example Markov random fields or variational optimization of a functional.

For example, the regularized map, e.g. the bone and hard plaque map, may be restored using an optimization of a functional in which the probability map is used as a fidelity term of the functional. The regularized map $\hat{R}$ may, for example, be obtained by optimizing the following functional:

$$\hat{R} = \underset{R}{\operatorname{argmin}} \int |\nabla_s R|^2 + \alpha \int |\nabla R| + \frac{1}{2}\lambda \int prob(\text{Map}_{ca} - R)^2 + \beta \int |R|$$

where $\nabla_s$ is the gradient of the cross section of the volume corresponding to the second value referred to hereinabove, e.g. the orientation of a surface template for which a maximum value was obtained in the computation of $prob_i^{ncc}$. In this exemplary functional, $\alpha$, $\lambda$ and $\beta$ are control parameters that may be predetermined or finetuned to provide a suitable trade-off between the functional terms, e.g. to select a suitable level of penalization of the regularization penalties referred to hereinabove in conjunction with a suitable level of fidelity to the probability map previously computed by the probability processor 13.

Such functional may be optimized using a conjugate gradient algorithm or a lagged diffusivity fixed point algorithm, such as known in the art, for example as described by Vogel in "Computational Methods for Inverse Problems", SIAM, 2002.

Furthermore, an iterative regularization procedure may be used, such as disclosed by Osher et al in "An iterative regularization method for total variation-based image restoration," Multiscale Modeling & Simulation 4.2 (2005): 460-489. For example, in a two iterations approach, the functional may be resolved a first time followed by a second time, where in the second iteration $2\text{Map}_{ca}-\hat{R}$ may be used as input to the fidelity term instead of $\text{Map}_{ca}$, in which $\hat{R}$ refers to the restored map obtained by the first iteration.

The image processing device further comprises a segmentation unit 14 for segmenting bone and/or hard plaque structures in the volumetric image data based on the probability map, e.g. based on the regularized map, calculated by the probability processor. In embodiments in accordance with the present invention, the segmentation unit may segment the bone and/or hard plaque structures based indirectly on the probability map, e.g. based directly on the regularized map.

For example, the segmentation unit may be adapted for applying a geometric active contour approach to the restored bone and hard plaque map. It is an advantage of such geometric active contour approach that the global shape of the bones and/or hard plaques may be captured in a robust manner.

For example, a segmentation $\hat{C}$ may be obtained by solving the following functional:

$$\hat{C} = \underset{C}{\operatorname{argmin}} \int_C g(\nabla \hat{R}) ds$$

where C represents the segmentation, e.g. in the form of a closed boundary curve, g(·) refers to an edge indicator function, such as $$g(x) = \frac{1}{1 + \gamma |x|^2}$$

and $\gamma$ is a control parameter. Such optimization could be carried out, for example, by a method known in the art, such as disclosed by Caselles et al in "Geodesic active contours," IEEE International Conference on Computer Vision, p. 694 (1995).

In a second aspect, embodiments of the present invention also relate to a computed tomography workstation comprising an image processing device in accordance with embodiments of the first aspect of the present invention. For example, embodiments of the present invention may relate to a workstation such as the computing system 116 described further herein below in relation to FIG. 2.

In a third aspect, embodiments of the present invention also relate to a spectral computed tomography system comprising an image processing device in accordance with embodiments of the first aspect of the present invention. For example, embodiments of the present invention may relate to a spectral computed tomography system such as the imaging system 100 described herein below in relation to FIG. 2.

Figure 2:
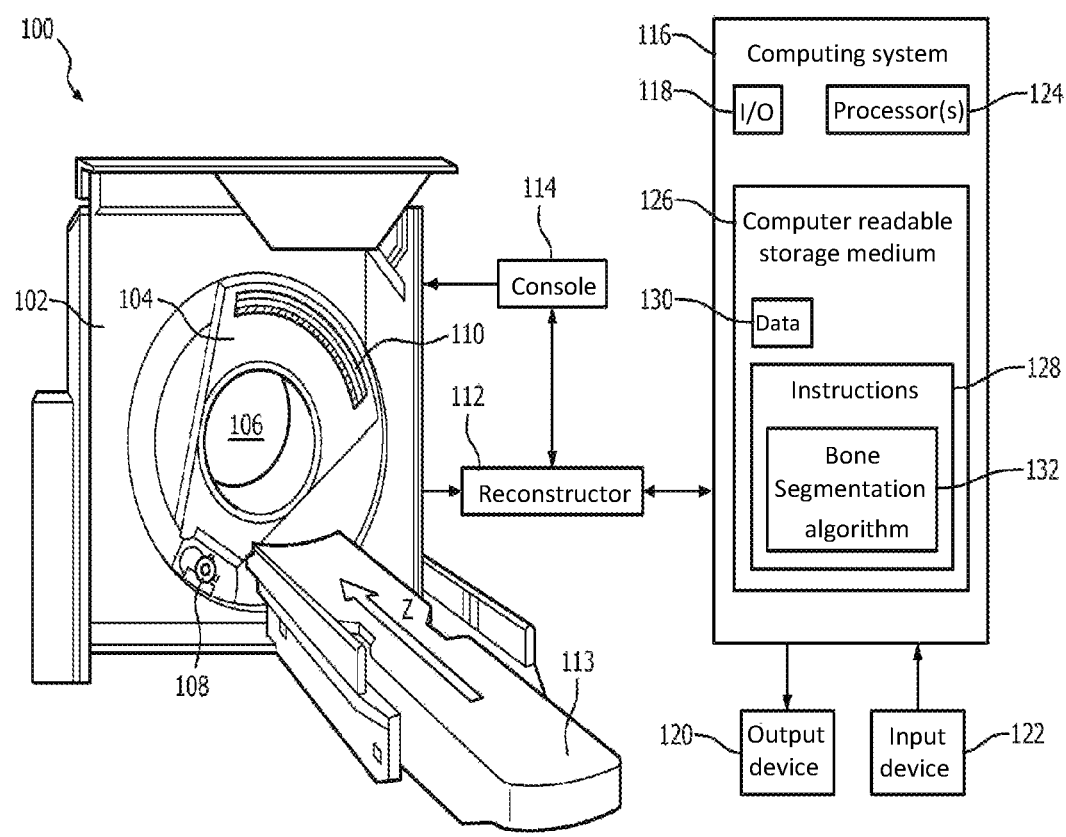
FIG. 2 schematically illustrates an imaging system comprising an image processing device in accordance with embodiments of the present invention.

FIG. 2 illustrates an imaging system 100 comprising a spectral computed tomography (Spectral CT) scanner. The imaging system 100 may comprise a generally stationary gantry 102 and a rotating gantry 104. The rotating gantry 104 may be rotatable supported by the stationary gantry 102 and may rotate around an examination region 106 about a longitudinal axis Z.

A radiation source 108, such as an x-ray tube, may be rotatable supported by the rotating gantry 104, e.g. such as to rotate with this rotating gantry 104, and may be adapted for emitting poly-energetic radiation that traverses the examination region 106. The radiation source 108 may comprise, or consist of, a single broad spectrum x-ray tube. Alternatively, the radiation source may be adapted for controllably switching between at least two different photon emission spectra, e.g. switching between at least two different peak emission voltages, such as 80 kVp, 140 kVp, etc., during scanning In another variation, the radiation source 108 may comprise two or more x-ray tubes configured to emit radiation with different mean spectrums. In another variation, the radiation source 108 may comprise a combination of the above.

A radiation sensitive detector array 110 may subtend an angular arc opposite the radiation source 108 across the examination region 106. The array 110 may include one or more rows of detectors arranged with respect to each other along the Z-axis direction. The array 110 may be adapted for detecting radiation traversing the examination region 106, and generating signals indicative thereof. The array 110 may comprise a dual-energy detector with at least two radiation sensitive detector elements having different x-ray energy sensitivities, e.g. at least two scintillators and at least two corresponding photosensors having corresponding optical sensitivities. The radiation sensitive detector array 110 may alternatively or additionally comprise a direct conversion detector, such as a CdTe, CdZnTe or other direct conversion detector known in the art.

The system may comprise a reconstructor 112 for reconstructing the signals output by the detector array 110. This may include decomposing the signal into various energy dependent components. The reconstructor 112 may be adapted for reconstructing the energy dependent components and generating one or more images corresponding to one or more different energies. The reconstructor 112 may also combine the energy dependent components to generate non-spectral image data.

The system may comprise a subject support 113, such as a couch, for supporting an object or subject in the examination region. The system may also comprise an operator console 114, e.g. a general purpose computer programmed for controlling or monitoring the system 100 and/or for providing a user interface for an operator. The console 114 may include a human readable output device such as a monitor or display and an input device such as a keyboard and mouse. Software resident on the console 114 may allow the operator to interact with the scanner 100 via a graphical user interface (GUI) or otherwise. This interaction may include selecting a spectral imaging protocol or a non-spectral imaging protocol, initiating scanning, etc.

The imaging system 100 may be operably connected to a workstation, e.g. computing system 116, such as a computer, that may comprise an input/output (I/O) interface 118 for facilitating communication with the spectral CT scanner. The imaging system 100 may comprise the computing system 116 as a system-level integrated component, or the imaging system 100 may be adapted for communicating with a stand-alone computing system 116, e.g. to transmit image data to the computing system 116.

The computing system 116 may further comprise an output device 120. The output device or output devices may comprise, for example, a display monitor, a film printer, a paper printer and/or an audio output for audio feedback. The computing system may also comprise an input device 122 or input devices, such as a mouse, a keyboard, a touch interface and/or a voice recognition interface. The computing system 116 may also comprise at least one processor 124, such as a central processing unit (CPU), a microprocessor, a dedicated application-specific integrated circuit (ASIC) for processing and/or an appropriately configured programmable hardware processor such as a field-programmable gate array. The computing system may comprise a computer readable storage medium 126, e.g. a non-transitory memory such as a physical digital memory. The computer readable storage medium 126 may store computer readable instructions 128 and data 130. The at least one processor 124 may be adapted for executing the computer readable instructions 128. The at least one processor 126 may also execute computer readable instructions carried by a signal, carrier wave or other transitory medium. Alternatively or additionally, the at least one processor may be physically configured to embody the instructions 128, e.g. entirely or in part, without necessarily requiring memory storage of these instructions, e.g. by configuration of a field-programmable gate array or an ASIC specifically designed to carry out at least a part of the instructions.

The computing system may be programmed, e.g. in accordance with the computer readable instructions referred to hereinabove, to implement an image processing device in accordance with embodiments of the first aspect of the present invention.

The instructions 128 may comprise an image processing algorithm 132 for performing a method in accordance with embodiments of a fourth aspect of the present invention.

In a fourth aspect, embodiments of the present invention also relate to a method for processing spectral computed tomography volumetric image data. This method comprises the step of obtaining spectral computed tomography volumetric image data organized in voxels, the volumetric image data comprising multispectral information for each voxel. The method further comprises estimating, for each voxel of the volumetric image data and based on the multispectral information, a first value indicative of a maximum probability that a local neighborhood around that voxel corresponds to a calcium surface structure and a second value indicative of an orientation of this calcium surface structure corresponding to that maximum. The method further comprises calculating a probability map indicative of a probability, for each voxel of the volumetric image data, that the voxel represents a bone or hard plaque structure, taking at least the first value, the second value and the multispectral information into account in this calculation. The method also comprises segmenting bone and/or hard plaque structures in the volumetric image data based on the probability map.

Details of methods in accordance with embodiments of the present invention shall be clear in relation to the description provided hereinabove relating to embodiments of the first aspect of the present invention. Particularly, functions performed by the data input, the calcium surface feature analyzer, the probability processor and/or the segmentation unit of a device in accordance with embodiments of the present invention shall be understood as constituting corresponding steps and/or features of a method in accordance with embodiments of the present invention.

Figure 3:
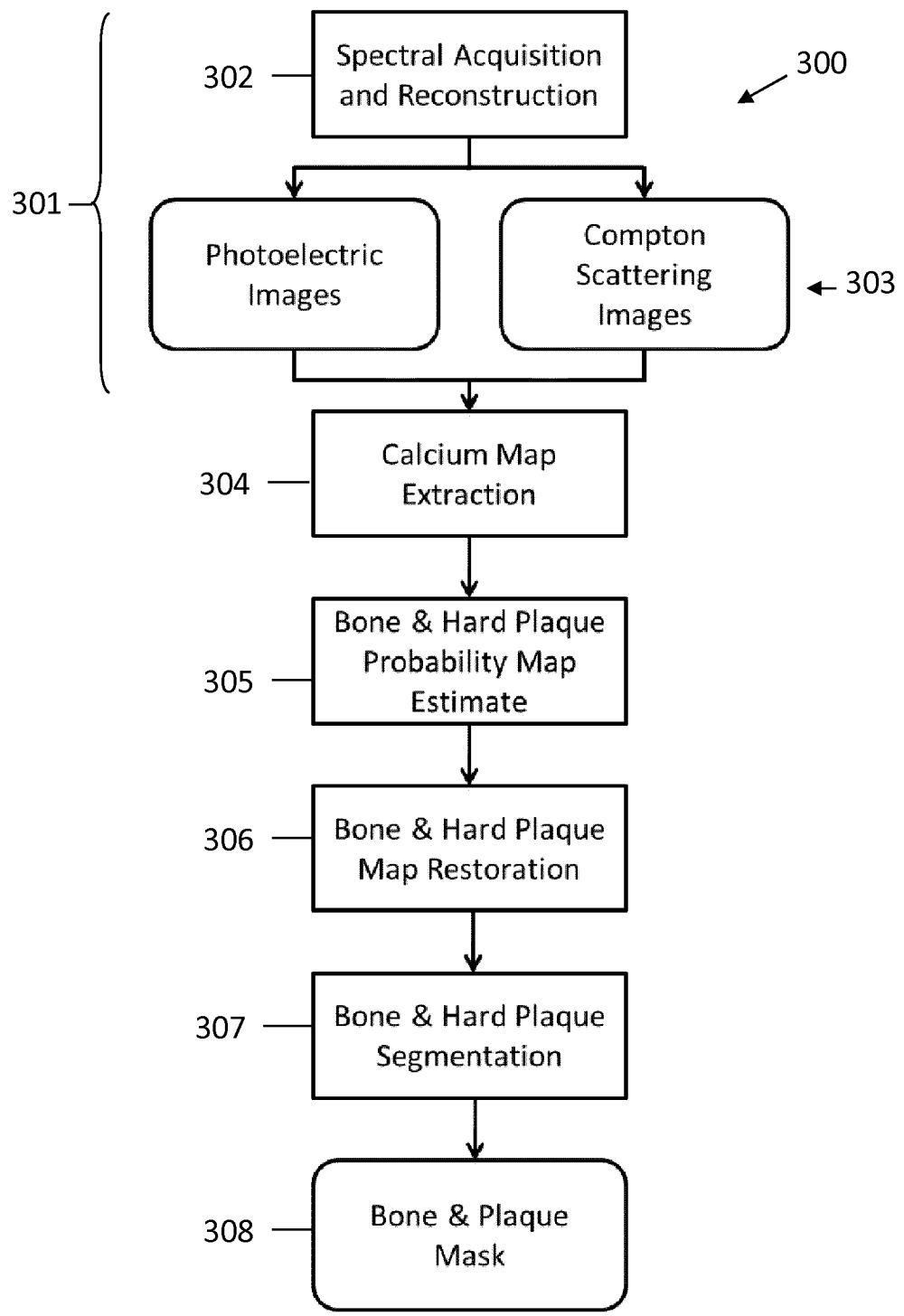
FIG. 3 schematically illustrates a method in accordance with embodiments of the present invention.

FIG. 3 illustrates an exemplary method 300 in accordance with embodiments of the present invention.

The method 300 comprises a step of obtaining 301 spectral computed tomography volumetric image data organized in voxels. For example, this step may comprise a spectral acquisition and a tomographic reconstruction 301, e.g. as known in the art and/or explained in more detail in relation to the imaging system shown in FIG. 2. This may result in a pair of images 303 representative of a different spectral content with respect to each other, such as photoelectric images and Compton scattering images.

The method 300 further comprises estimating, for each voxel of the volumetric image data, a first value indicative of a maximum probability that a local neighborhood around that voxel corresponds to a calcium surface structure and a second value indicative of an orientation of this calcium surface structure corresponding to that maximum. For example, the method 300 may comprise generating a calcium map 304 based on the volumetric image data, wherein the calcium map comprises, for each voxel of the volumetric image data, a value indicative of a calcium content at the corresponding voxel location, and calculating the first and second value based on this calcium map.

The method further comprises calculating a probability map 305 indicative of a probability, for each voxel of the volumetric image data, that the voxel represents a bone or hard plaque structure, taking at least the first value and the second value into account in this calculation.

Furthermore, the method may comprise calculating a regularized map based on said probability map, e.g. performing a bone and hard plaque map restoration 306.

The method also comprises segmenting 307 bone and/or hard plaque structures in the volumetric image data based on the probability map, e.g. based on the regularized map.

The method may also comprise outputting 308 the bone and/or hard plaque map obtained by this segmentation 307.

In a fifth aspect, embodiments of the present invention also relate to a computer readable storage medium encoded with one or more computer executable instructions, which, when executed by a processor of a computing system causes the computing system to perform a method in accordance with embodiments of the fourth aspect of the present invention.

Figure 4:
FIG. 4 to FIG. 11 show a first exemplary application of contrast-enhanced liver imaging using dual energy CT, relating to embodiments of the present invention.
Figure 5:
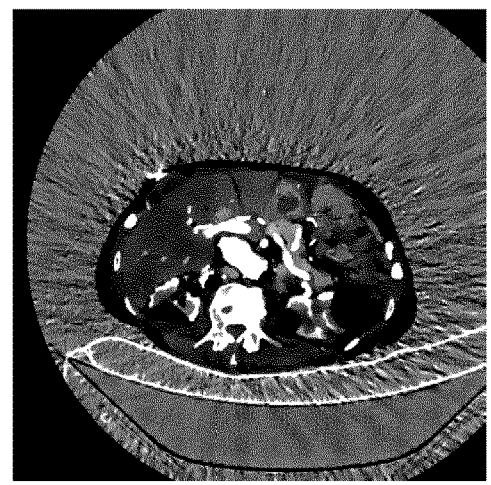
Figure 6:
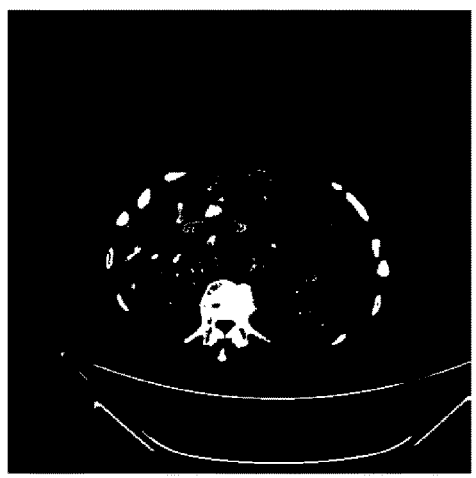
Figure 7:

In a first example illustrating embodiments of the present invention, FIG. 4 to FIG. 11 illustrate an application of contrast-enhanced liver imaging using dual energy CT. FIG. 4 shows a conventional CT image of the abdominal region. FIG. 5 shows an image of the same region obtained by spectral CT, showing the spectral calcium image component without the spectral image component of soft tissue. This image shows the remaining iodine component in organs, and particularly, in the major blood vessels. FIG. 6 shows a linear separation map of calcium, providing a better suppression of the iodine contrast agent, yet showing remaining artefacts of iodine in the linear separation map. FIG. 7 shows a linear segmentation of the bone structures based on the linear separation map of FIG. 6, as could be obtained by a prior art segmentation method, overlaid on an anatomical reference image. Several segmentation misclassifications can be observed in FIG. 7, such as the region 71.

Figure 8:
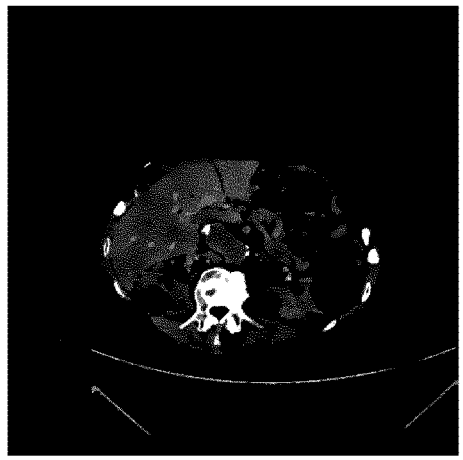
Figure 9:
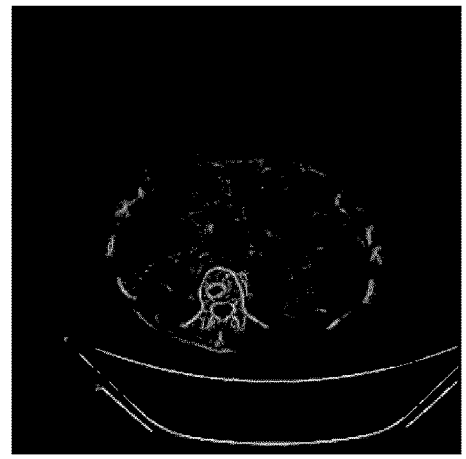

FIG. 8 shows a calcium map, as obtainable in a step of a method in accordance with embodiments of the present invention, e.g. a map estimated as the minimum between projections along the calcium line to the soft tissue line and the iodine line, as described hereinabove. FIG. 9 shows a probability map as obtainable in a step of a method in accordance with embodiments of the present invention, e.g. by applying a multiscale approach $$\text{prob} = \max_i \{\text{prob}_i\}_{i=1}^n,$$

where the probability at scale I, e.g. scaled down by a factor $(\frac{1}{2})^{i-1}$, may be calculated by a voxel wise product, i.e. Hadamard product:

$$\text{prob}_i = \text{prob}_i^{calio} \cdot \text{prob}_i^{ncc} \cdot \text{prob}_i^{ridge} \cdot \text{prob}_i^{texture} \cdot \text{prob}_i^{dist}.$$

The surface enhancement provided by, at least, the $\text{prob}_i^{ncc}$ and $\text{prob}_i^{ridge}$ factors in this product can be clearly observed, whereas the $\text{prob}_i^{texture}$ and $\text{prob}_i^{dist}$ factors may advantageously provide an additional robustness to input image noise. Furthermore, the multiscale approach allows, at least, the surface enhancement factors to be less dependent on scale variations in bone and plaque structures and on the surface curvature associated therewith.

Figure 10:
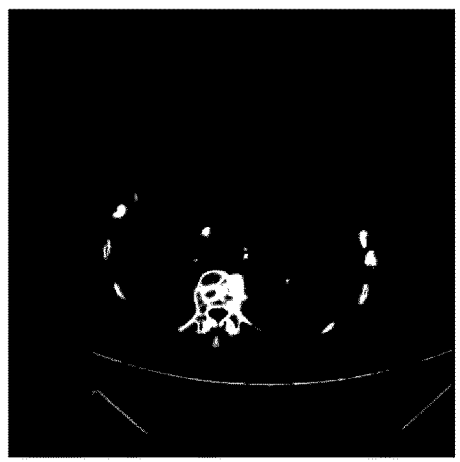
Figure 11:
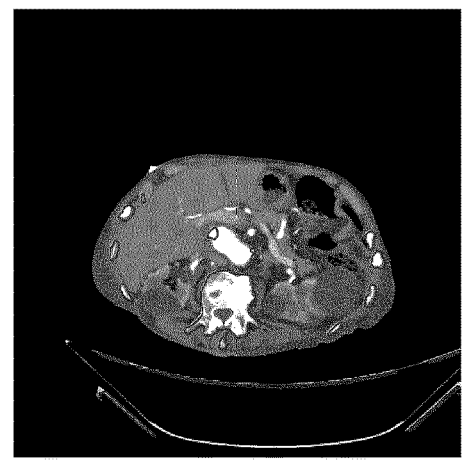

Referring to FIG. 10, the result of an additional regularized optimization of the probability map is shown, in accordance with embodiments of the present invention. For example, this restored map may be obtained by optimizing the functional $$\hat{R} = \underset{R}{\operatorname{argmin}} \int |\nabla_s R|^2 + \alpha \int |\nabla R| + \frac{1}{2}\lambda \int prob(\text{Map}_{ca} - R)^2 + \beta \int |R|$$

as described hereinabove. FIG. 11 shows, overlaid on an anatomical reference image, a result of a segmentation in accordance with embodiments of the present invention, e.g. as obtainable by applying an active contour detection on the restored map. When comparing FIG. 11 to FIG. 7, substantially less misclassification of non-bone areas can be observed for the segmentation in accordance with embodiments of the present invention.

Figure 12:
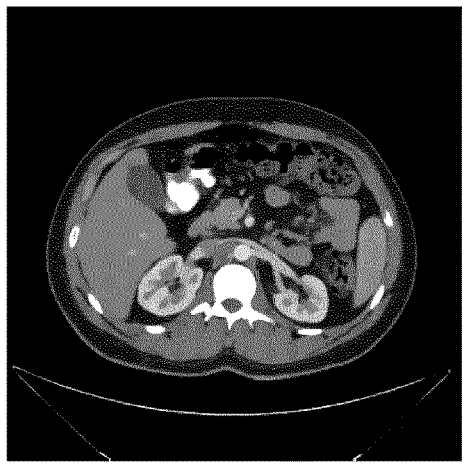
FIG. 12 to FIG. 19 show a second exemplary application of contrast-enhanced kidney and liver imaging using dual energy CT, relating to embodiments of the present invention.
Figure 13:
Figure 14:
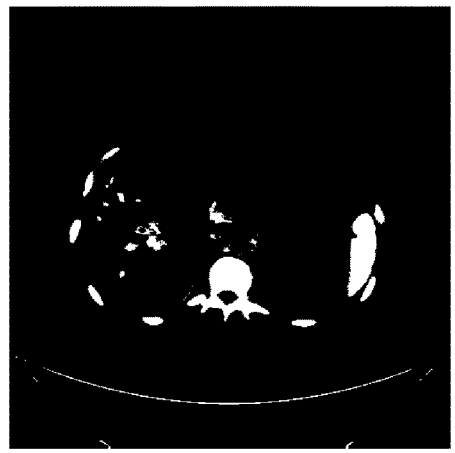
Figure 15:

In a second example illustrating embodiments of the present invention, FIG. 12 to FIG. 19 illustrate an application of contrast-enhanced kidney and liver imaging using dual energy CT. FIG. 12 shows a conventional CT image of the abdominal region. FIG. 13 shows an image of the same region obtained by spectral CT, showing the spectral calcium image component without the spectral image component of soft tissue. This image shows the remaining iodine component in organs, and particularly, in the kidneys. FIG. 14 shows a linear separation map of calcium, providing a better suppression of the iodine contrast agent, yet showing remaining artefacts of iodine in the linear separation map. FIG. 15 shows a linear segmentation of the bone structures based on the linear separation map of FIG. 14, as could be obtained by a prior art segmentation method, overlaid on an anatomical reference image.

Figure 16:
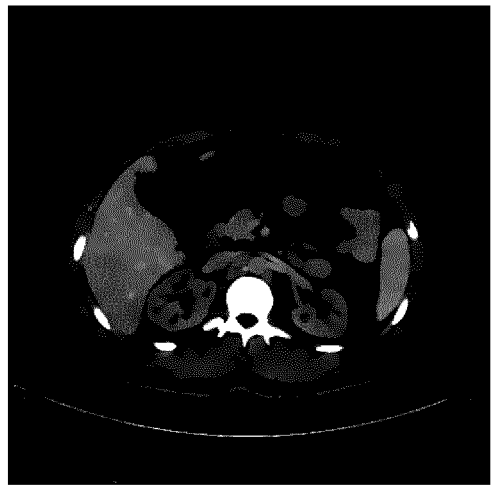
Figure 17:

FIG. 16 shows a calcium map, as obtainable in a step of a method in accordance with embodiments of the present invention, e.g. a map estimated as the minimum between projections along the calcium line to the soft tissue line and the iodine line, as described hereinabove. FIG. 17 shows a probability map as obtainable in a step of a method in accordance with embodiments of the present invention, e.g. obtainable by an approach like what was described in the first example.

Figure 18:
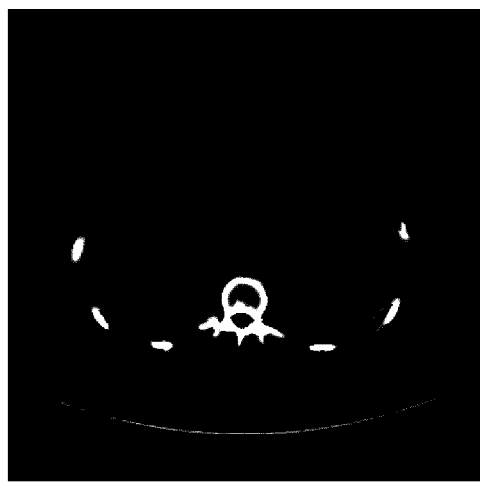
Figure 19:
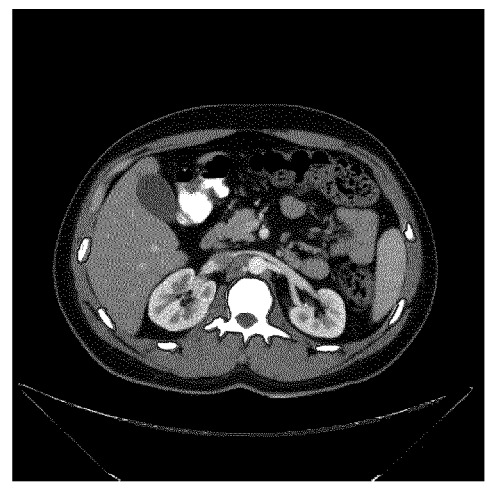

Referring to FIG. 18, the result of an additional regularized optimization of the probability map is shown, in accordance with embodiments of the present invention, e.g. as described in previous example. FIG. 19 shows, overlaid on an anatomical reference image, a result of a segmentation in accordance with embodiments of the present invention, e.g. as obtainable by applying an active contour detection on the restored map of FIG. 18. When comparing FIG. 18 to FIG. 14, substantially less misclassification of non-bone areas can be observed for the segmentation in accordance with embodiments of the present invention.

The invention claimed is:

1. An image processing device, comprising:
   a data input for receiving spectral computed tomography volumetric image data organized in voxels, wherein said volumetric image data comprises multispectral information for each voxel;
   a calcium surface feature analyzer for estimating, for each voxel of said volumetric image data and based on said multispectral information, a first value indicative of a maximum probability that a local neighborhood around said voxel corresponds to a calcium surface structure and a second value indicative of an orientation of said calcium surface structure that corresponds to said maximum;
   a probability processor for calculating a probability map indicative of a probability, for each voxel of said volumetric image data, that said voxel represents a bone or hard plaque structure, taking at least said first value, said second value and said multispectral information into account; and
   a segmentation unit for segmenting at least one of a bone structure and a hard plaque structure in said volumetric image data based on said probability map.

2. The image processing device of claim 1, wherein said probability processor and said calcium surface feature analyzer are configured to perform a multi-scale analysis, wherein the probability, for each voxel of the volumetric image data, that the voxel represents a bone or hard plaque structure is determined at a plurality of different scales, and the probability map is determined by, for each voxel, selecting the maximum probability over said plurality of different scales.

3. The image processing device of claim 1, wherein said calcium surface feature analyzer is configured to generate a calcium map based on said multispectral information for each voxel in said volumetric image data, wherein the calcium map comprises, for each voxel of the volumetric image data, a value indicative of a calcium content at the corresponding voxel location, and wherein said first value and said second value are estimated based on said calcium map.

4. The image processing device of claim 3, wherein said calcium surface feature analyzer is further configured to determine the first value, for each voxel, as a maximum of probabilities, wherein each of said probabilities represents a probability of the local neighborhood around said voxel in said calcium map to match a corresponding predetermined surface template.

5. The image processing device of claim 1, wherein the probability processor is configured to determine said probability, for each voxel of the volumetric image data, that the voxel represents a bone or hard plaque structure by combining a plurality of probabilities indicative of spectral information and morphological features around each voxel.

6. The image processing device of claim 5, wherein the probability processor is configured to combine said plurality of probabilities by multiplication.

7. The image processing device of claim 5 wherein said probability processor is configured to combine said plurality of probabilities for each scale of said plurality of scales separately.

8. The image processing device of claim 5, wherein said probability processor is configured to compute said plurality of probabilities indicative of spectral information and morphological features around each voxel, the plurality of probabilities comprising said first value indicative of the maximum probability that a local neighborhood around the voxel corresponds to a calcium surface structure and at least one of:
   a probability of the voxel being at a volumetric ridge in the calcium map taking said second value into account,
   a probability of the voxel to include calcium and not iodine, based on said multispectral information,
   a probability that a neighborhood of the voxel has a spectral response that is different from a spectral response of iodine, based on said multispectral information, and
   a probability of a neighborhood of the voxel to have a bone or a hard plaque texture.

9. The image processing device of claim 1, wherein said probability processor is furthermore configured to calculate a regularized map based on said probability map, wherein calculating said regularized map comprises a joint optimization of at least:
   a fidelity measure representative of a difference between said regularized map and said probability map, and
   a regularization penalty.

10. The image processing device of claim 9, wherein said regularization penalty comprises at least one of:
   a penalty for inhomogeneous spatial distribution of the regularized map,
   a penalty for inhomogeneous spatial distribution of the gradient magnitude of the regularized map, and
   a penalty for local inhomogeneity of the regularized map along the local surface orientation defined by said second value.

11. The image processing device of claim 9, wherein said probability processor is configured to calculate said regularized map using variational optimization of a functional.

12. The image processing device of claim 9, wherein said segmentation unit is configured to apply a geometric active contour approach to said regularized map.

13. A computed tomography workstation comprising an image processing device in accordance with claim 1.

14. A method for processing spectral computed tomography volumetric image data, the method comprising:
   obtaining spectral computed tomography volumetric image data organized in voxels, wherein said volumetric image data comprises multispectral information for each voxel;
   estimating, for each voxel of said volumetric image data and based on said multispectral information, a first value indicative of a maximum probability that a local neighborhood around said voxel corresponds to a calcium surface structure and a second value indicative of an orientation of said calcium surface structure that corresponds to said maximum;
   calculating a probability map indicative of a probability, for each voxel of said volumetric image data, that said voxel represents a bone or hard plaque structure, taking at least said first value, said second value and said multispectral information into account; and
   segmenting at least one of a bone structure and a hard plaque structure in said volumetric image data based on said probability map.

15. A non-transitory computer-readable medium having one or more executable instructions stored thereon, which, when executed by a processor, cause the processor to perform a method for processing spectral computed tomography volumetric image data, the method comprising:
   obtaining spectral computed tomography volumetric image data organized in voxels, wherein said volumetric image data comprises multispectral information for each voxel;
   estimating, for each voxel of said volumetric image data and based on said multispectral information, a first value indicative of a maximum probability that a local neighborhood around said voxel corresponds to a calcium surface structure and a second value indicative of an orientation of said calcium surface structure that corresponds to said maximum;
   calculating a probability map indicative of a probability, for each voxel of said volumetric image data, that said voxel represents a bone or hard plaque structure, taking at least said first value, said second value and said multispectral information into account; and
   segmenting at least one of a bone structure and a hard plaque structure in said volumetric image data based on said probability map.

* * * * *